United States Patent
Brown et al.

(10) Patent No.: US 7,691,397 B2
(45) Date of Patent: *Apr. 6, 2010

(54) ULTRA-STABLE COMPOSITION COMPRISING MORINGA OIL AND ITS DERIVATIVES AND USES THEREOF

(75) Inventors: James H. Brown, Scottsdale, AZ (US); Robert Kleiman, Sun Lakes, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 1539 days.

This patent is subject to a terminal disclaimer.

(21) Appl. No.: 10/410,787

(22) Filed: Apr. 8, 2003

(65) Prior Publication Data

US 2003/0198629 A1    Oct. 23, 2003

Related U.S. Application Data

(63) Continuation-in-part of application No. 09/964,988, filed on Sep. 26, 2001, now Pat. No. 6,667,047, which is a continuation-in-part of application No. 09/917,091, filed on Jul. 27, 2001, now Pat. No. 6,528,075.

(51) Int. Cl.
*A61K 8/02* (2006.01)
*A61K 8/92* (2006.01)

(52) U.S. Cl. .................. 424/401; 424/776; 514/844

(58) Field of Classification Search .............. None
See application file for complete search history.

(56) References Cited

U.S. PATENT DOCUMENTS

| | | | |
|---|---|---|---|
| 3,384,545 A * | 5/1968 | Bauernfeind et al. | 514/167 |
| 5,077,069 A | 12/1991 | Chang et al. | |
| 5,263,478 A | 11/1993 | Davis | |
| 5,279,610 A | 1/1994 | Park et al. | |
| 5,660,865 A | 8/1997 | Pedersen | |
| 5,683,683 A | 11/1997 | Scafidi | |
| 5,749,357 A | 5/1998 | Linder | |
| 6,286,509 B1 | 9/2001 | Nash et al. | |
| 6,287,579 B1 | 9/2001 | Kleiman et al. | 424/401 |
| 6,348,200 B1 | 2/2002 | Nakajima | |
| 6,528,075 B1 | 3/2003 | Brown et al. | 424/401 |
| 6,667,047 B2 | 12/2003 | Brown et al. | |

FOREIGN PATENT DOCUMENTS

| | | |
|---|---|---|
| EP | 0326829 | 8/1989 |
| JP | 52-136933 | * 11/1977 |
| JP | 57-179297 | * 11/1982 |
| JP | 57179297 | 11/1982 |
| JP | H05156248 A | 6/1993 |
| WO | WO 00/76464 | 12/2000 |
| WO | 02096225 A2 | 12/2002 |
| WO | WO 03/011234 | 2/2003 |

OTHER PUBLICATIONS

M-C Martini et al.: "Actifs et additifs en cosmetologie" 1993, Lavoisier Tec & Doc, FR 196800, pp. 30, 224, 225.
R. Rosenwald: "Antioxidants and control of oxidative deterioration of cosmetics", American Perfumer and Cosmetics, vol. 78, No. 10, 1963, pp. 41-44.
H. Le Poole, "Behen oil: a clasic oil for modern cosmetics," Cosmetics&Toiletries Magazine, vol. 111, Jan. 1996, pp. 77-80.
P. Delaveau, "Huiles de Moringa oleifera Lamk. et de M. Drouhardii Jumelle," Plantes Medicinales et Phytotherapie, vol. XIV, No. 1. pp. 29-33, 1980.
JP Sutherland, Moringa Oil, The ancient of oils, Soap Perfum Cosmetics, May 2001, pp. 48-50.
Japan Patent Office, Yumi Takaoka, Third Patent Examination Department, Medical Science Division, "Notice of Reasons for Rejection," Japanese Patent Appln. No. 2003-516466, mailed Jan. 11, 2008.
Hiroshi Hirota, "The Science of Fats and Fatty Oils for Cosmetics," Fragrance Journal Limited, Apr. 10, 2001, Second Edition, pp. 155-185 (Chapter 4: Aging of Fatty Oils and its Prevention). [No English Translation Available] Concise Explanation of Relevance pursuant to 37 CFR §1.98(a)(3)(i): This article (the "Hirota article") was cited by the Japanese Patent Examiner in the Jan. 11, 2008 Japanese Office Action, an English translation of which is provided. The relevance, if any, of the Hirota article is set forth in the Japanese Office Action.
European Patent Office "Decision Refusing European Patent Application No. 02 756 420.2," Jan. 15, 2007.
Japan Patent Office "Notice of Reasons for Rejection," Sep. 2, 2009; Japan Patent Application No. 2004-553537.

* cited by examiner

*Primary Examiner*—Phyllis G. Spivack
(74) *Attorney, Agent, or Firm*—Ingrassia Fisher & Lorenz, P.C.

(57) ABSTRACT

Compositions may include long-chain organic molecules obtained from natural oils, particularly plant, bean, seed and nut oils, and their derivatives can be provided with increased oxygen stability by their combination with mixtures of particular classes of antioxidants, particularly combinations of at least one synthetic free-radical terminating antioxidant. The stabilization combination is particularly effective in combination with long-chain oils having less than 5% methylene interrupted unsaturation and free-radical terminating antioxidants present in an amount of from 0.001 to 5% or more by weight of the long-chain oils. The long-chain oil may include a natural oil or wax, such as Macadamia oil and its derivatives, Moringa oil and its derivatives, Babassu oil and its derivatives, Meadowfoam oil and its derivatives, and High Oleic Sunflower oil.

6 Claims, No Drawings

US 7,691,397 B2

ULTRA-STABLE COMPOSITION COMPRISING MORINGA OIL AND ITS DERIVATIVES AND USES THEREOF

This application is a continuation-in-part of application Ser. No. 09/964,988, which was filed on Sep. 26, 2001, now U.S. Pat. No. 6,667,047 which was a continuation-in-part of application Ser. No. 09/917,091, which was filed on Jul. 27, 2001 and issued as U.S. Pat. No. 6,528,075 on Mar. 4, 2003.

FIELD OF THE INVENTION

The present invention relates to ultra-stable long chain oils, particularly long chain oils used in conjunction with cosmetic and pharmaceutical products that are externally applied to patients. The present invention particularly relates to the provision of oxidatively ultra-stable emollients produced when free-radical terminating antioxidants are added to natural oils and waxes, and their derivatives, having a percentage of methylene unsaturation less than 5%.

BACKGROUND

Emollients are materials that are applied to the skin of subjects to produce softness or smoothness. They have been used for centuries in both cosmetic and pharmaceutical products. The original emollients were extracts or directly concentrated materials from plants or animals, while modern emollients also include partially synthetic (derivatives of natural products) or completely synthetic materials.

In addition to the feel of an emollient upon application to the skin, cosmetics and their ingredients must exhibit stability, both in storage and in use. The cosmetics must not deteriorate or separate in storage and use, and the individual ingredients should not decompose or otherwise undergo chemical changes that alter their desirable properties. One of the more common susceptibilities of products or components to ambient damage is from oxidation, and natural materials are clearly, through observation, susceptible to oxidation, as is commonly seen by browning of fruit exposed to air or the rancid smell of old vegetable oils. Many foods, food additives, cosmetics, fragrances, medicaments, and colorants are well known to be subject to damaging effects from oxidation.

The most frequent means of reducing the effects of oxidation (including light amplified or stimulated oxidation) include oxygen excluding packaging (e.g., bottles, cans, oxygen impermeable polymer wraps, and the like), chemical modifications of the ingredient to reduce its tendency toward oxidation while minimally altering its functional properties, and the addition of antioxidants to directly quench oxidative species before they oxidize the ingredient. Packaging controls are most effective where a product is to be used once, as when the package is opened, air is introduced into the container and the package provides no complete protection against contact with oxygen. Chemical modification of an ingredient offers more general protection, assuming that a modification can be devised that both substantially reduces the tendency towards oxidation and also maintains the functional properties desired in the selection of the underlying chemical. This can be an exhaustive task, with no guarantees of success.

The use of antioxidants offers a general approach to the oxidation problem for a wide variety of materials and fields including the protection of edible materials against premature oxidation. The use of antioxidants would appear to some to require little more than the appropriate selection of an antioxidant sold commercially for specific purposes to achieve a commercially viable product with a necessary level of oxidation resistance. However, antioxidants may have and often display unique interaction with other ingredients and with the primary component on either a physical level (by not blending with the other materials), on a chemical level (by reaction with active ingredients), or both. It is therefore necessary, with some compositions that require antioxidant protection, to conduct extensive research with no assurance of success. There are also such a wide variety of classes of antioxidants and so many variants within the classes that a search for an appropriate antioxidant is a highly problematic search, and the desire for the best antioxidant assures a time consuming process.

Among the more common classes of antioxidants are free-radical terminators, particularly those with available hydrogens from phenolic hydroxyl groups. Within that single class are the subclasses of butylated hydroxyanisole (BHA) and butylated hydroxytoluene (BHT), hydroquinones (such as tertiary-butylhydroquinones, and propyl gallate). Reducing agents or oxygen scavengers encompass another class of antioxidants and includes ascorbic acid (vitamin C) and its derivatives (such as esters of ascorbic acid, such as ascorbyl palmitate); sulfites (such as sulfur sulfite, alkali metal sulfites, and bisulfites, including alkali metal bisulfites); glucose oxidases (including catalase); erythorbic acid and its derivatives. Chelating agents comprise another class of materials that have been used to address problems with potentiators of oxidation and include citric acid (and its derivatives), polyphosphages, and aminopolycarboxylic acids (such as ethylenediaminetetraacetic acid (EDTA). Finally, there are other antioxidant classes with less general areas of use.

The use of polyglycerol esters as oil in water (o/w) emulsifiers for cosmetic formulations is described, for example, in J. Soc. Cosmet. Chem. 28, 733-740 (1977) and in Fette, Seifen, Anstrichmettel 88, 101-106 (1986). In addition, the use of selected polyglycerol fatty acid esters as cosmetic emulsifiers is claimed in DE-A1 40 05 819 and DE-A1 40 23 593 (BASF). However, in cases where the esters based on unsaturated or saturated fatty acids mentioned in these documents are used, it has been found that the resulting emulsions are not always sufficiently stable in storage. The invention of that reference relates to cosmetic and/or pharmaceutical formulations that are characterized in that they contain monoesters of triglycerol with saturated $C_{16}$-$C_{18}$ fatty acids as emulsifiers, the monoester content being from 30-50% by weight. It was asserted that it was surprising that the degree of self-condensation of the oligoglycols in conjunction with the nature of the fatty acid and the percentage content of monoesters has a bearing on the properties of the resulting emulsifiers. That invention includes, in particular, the observation that the establishment of a percentage monoester content of 30-50% in the emulsifiers according to the invention leads to a significant improvement in stability compared with otherwise known products of the prior art.

In spite of this, there is a present and continuing need for a class of compositions comprising oils and waxes that exhibit extended stability relative to unadulterated oils and waxes alone.

SUMMARY OF INVENTION

It is an object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone.

It is another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone wherein the free radical-terminating antioxidant is present in an amount of from 0.001 to 5.0% by weight of said long chain oil.

It is yet another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone, wherein said long chain oil has a percent methylene interrupted unsaturation of less than 1%.

It is yet another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone, wherein said long chain oil is selected from the group consisting of moringa nut oil and its derivatives, macadamia nut oil and its derivatives, babassu nut oil and its derivatives, and meadowfoam oil and its derivatives.

It is a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone, where the long-chain oil has a slip value greater than that of castor oil, 7.0 as measured by a modified Cadicamo method.

It is yet a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone and further comprising a reducing agent present in an amount of from 0.001 to 2% by weight.

It is yet a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 400% relative to the oxidation stability of the oil alone and further comprising a reducing agent present in an amount of from 0.001 to 2% by weight, wherein the reducing agent is selected from the group comprising ascorbic acid and its derivatives; sulfites; glucose oxidases (including catalase); and erythorbic acid and its derivatives.

It is another object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone.

It is yet another object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone, wherein the free radical-terminating antioxidant is present in an amount of from 0.001 to 5.0% by weight of said long chain oil.

It is yet another object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone, wherein said long chain oil is selected from the group consisting of moringa nut oil and its derivatives, macadamia nut oil and its derivatives, babassu nut oil and its derivatives, and meadowfoam oil and its derivatives.

It is a further object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone, where the long-chain oil has a slip value greater than that of castor oil, 7.0 as measured by a modified Cadicamo method.

It is yet a further object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone and further comprising a reducing agent present in an amount of from 0.001 to 2% by weight.

It is yet a further object of the present invention to provide a composition comprising a long-chain oil, said long-chain oil has a percent methylene interrupted unsaturation of less than 1%, in combination with at least one free-radical terminating antioxidant, wherein said free-radical terminating antioxidant provides an oxidation stability to the long-chain oil of more than 400% relative to the oxidation stability of the oil alone and further comprising a reducing agent present in an amount of from 0.001 to 2% by weight, wherein the reducing agent is selected from the group comprising ascorbic acid and its derivatives; sulfites; glucose oxidases (including catalase); and erythorbic acid and its derivatives.

It is another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone.

It is yet another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, wherein the free radical-terminating antioxidant is present in an amount of from 0.001 to 5.0% by weight of said long chain oil.

It is yet another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, wherein said long chain oil has a percent methylene interrupted unsaturation of less than 1%.

It is a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, wherein said long chain oil is selected from the group consisting of moringa nut oil and its derivatives, macadamia nut oil and its derivatives, babassu nut oil and its derivatives, and meadowfoam oil and its derivatives.

It is yet a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, where the long-chain oil has a slip value greater than that of castor oil, 7.0 as measured by a modified Cadicamo method.

It is yet a further object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, further comprising a reducing agent present in an amount of from 0.001 to 2% by weight.

It is another object of the present invention to provide a composition comprising a long-chain oil, said long-chain oil has a percent methylene interrupted unsaturation of less than 5%, in combination with at least one free-radical terminating antioxidant, wherein said free-radical terminating antioxidant provides an oxidation stability to the long-chain oil of more than 1000% relative to the oxidation stability of the oil alone, further comprising a reducing agent present in an amount of from 0.001 to 2% by weight, wherein the reducing agent is selected from the group comprising ascorbic acid and its derivatives; sulfites; glucose oxidases (including catalase); and erythorbic acid and its derivatives.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

Compositions comprising long chain oils, or waxes, and their derivatives can be provided with a surprisingly large increase in oxidation stability by combination with mixtures of particular classes of synthetic antioxidants, particularly the combination with at least one synthetic free-radical terminating antioxidants, such as butylated hydroxyanisole (BHA) and butylated hydroxytoluene (BHT), hydroquinones (such as tertiary-butylhydroquinones, and propyl gallate). The stabilization combination, according to the present invention, is particularly effective when the long-chain oils have less than 5% methylene interrupted unsaturation. Further, this large increase can be supplemented by including a small amount of a reducing agent, or oxygen scavenger, to the composition.

Extension of the stability of oils and waxes containing low percentages of methylene interrupted unsaturation have been discussed in U.S. Pat. No. 6,287,579 (the '579 patent), which issued to Kleiman et al. on Sep. 11, 2001 and U.S. Pat. No. 6,528,075 (the '075 patent), which issued to Brown et al. on Mar. 4, 2003, the contents of which are both incorporated herein.

The '579 patent discloses that derivatives of natural oils, specifically the ethyl ester derivatives of oils and waxes having methylene interrupted unsaturation of less than 20% can be surprisingly extended by the addition of tocopherol (vitamin E) and a supplemental additive selected from the group consisting of kojic acid, malic acid, and ascorbic acid. By synergy, this combination of these two components enabled an increase of oxidative stability that was orders of magnitude greater than that enjoyed by unaltered oils and waxes.

However, what was not disclosed, and is not obvious to one of ordinary skill in the arts, is the extraordinary ultra-stability provided when synthetic free-radical terminating antioxidants are added to oils and waxes, and their derivatives, that have a methylene interrupted unsaturation of less than 5%. While tocopherol is a free-radical terminating antioxidant, it is a natural product that differs structurally from the synthetic free-radical terminating antioxidants by being bicyclic, with one of the two rings further being heteroatomic by containing oxygen.

Described herein, by way of example of the inventive composition, is a composition that is comprised of oil, or wax, or derivatives thereof, in combination with a synthetic free-radical terminating antioxidant, which provides unexpected oxidation stability to the oil or wax. The composition of the present invention is oxidatively ultra-stable relative to emollient compositions that do not include the synthetic free-radical terminating antioxidant of the present invention. Preferably, the oils or waxes, and their derivatives, are produced from natural products having a percent methylene interrupted unsaturation of less than 5%, such as moringa, macadamia, babassu, meadowfoam, high oleic sunflower, castor, coconut, jojoba, cuphea, dill seed, lunaria and various lauraceae oils. Herein, the term "long-chain oil of moringa" includes pure moringa oil and derivatives thereof. Herein, "derivatives" means oils, or waxes, produced from an original oil that are further processed, such as by making the methyl ester, the ethyl ester, the isopropyl ester, hydrogenated oils, and the like.

The characteristic of the degree of methylene interrupted unsaturation has some particular significance for the selection of preferred materials in the practice of the present invention, with those oils or waxes, and their derivatives, having less than 5% methylene interrupted unsaturation being most desirable. The term "percent methylene interrupted unsaturation" is used as a description of the internal structure of these various components of the oils, such as triglycerols and esters. The term literally means the weight percent of acyl groups having double bonds separated by or interrupted by a methylene group, —$CH_2$—. This term is used to better explain the reactivity of fatty acyl groups whose double bonds are so far away from one another that they behave chemically as monoenoic fatty acyl groups. For example, consider the double bonds at the delta-5 and delta-13 position of meadowfoam oil. The double bonds are so remote from each other that the acyl group acts as if it were monoenoic. The two double bonds do not interact in a way that would cause the fatty acid group to behave as a dienoic molecule rather than as a monoenoic molecule. The weight percent of acyl groups having double bonds separated by a methylene group is calculated, then added to other such acyl groups to determine the total percent methylene interrupted unsaturation. Soybean oil, for example, has two such acyl groups, linoleic and linolenic acids. The weight percentages of these two acyl groups in soybean oil are usually 52% and 6%, respectively. The percent methylene interrupted unsaturation is therefore 58%.

All oils or waxes, and their derivatives, oxidatively degrade. Their oxidative stability is measured and compared using an oil stability index (OSI, as outlined in The Official and Tentative Methods of the American Oil Chemists' Society, AOCS Method Cd 12b-92). Previously, the use of the most common antioxidants (e.g., BHA and BHT, for example) with these natural long-chain oils (e.g., from at least about 8 carbon atoms to 30 or more carbon atoms in the primary aliphatic chain) and their ethyl esters, fats or fatty materials were expected to slightly improve their oxidative stability, but not provide dramatic improvements in levels of OSI in these oils.

Table 1 reports the OSI values of a variety of different natural oils (as used herein the term "oils" includes waxes and fats), and select derivatives, both with and without free-radical terminating antioxidants, thereby illustrating the ultra-stabilization that the addition of synthetic free-radical terminating antioxidants provides. Further reported in Table 1 are the percent increases in stability provided by the addition of free-radical terminating antioxidants, and percent polyunsaturation of the different oils.

Pure moringa oil has an oxidative stability of 29.6 hours and a percentage methylene interrupted unsaturation of 0.7%. Pure meadowfoam oil has an oxidative stability of 69.1 hours and a percentage methylene interrupted unsaturation of 1.0%. Pure babassu oil has an oxidative stability of 46.5 hours and a percentage methylene interrupted unsaturation of 1.5% Pure macadamia oil has an oxidative stability of 5.6 hours and a percentage methylene interrupted unsaturation of 3.5%. According to data on other natural oils, these natural oils having a percentage methylene interrupted unsaturation of greater than 10.0%, the addition of small amounts of synthetic free-radical terminating antioxidants should increase the oxidative stability by under 400% or if one were to omit the data on High Oleic sunflower oil, one would expect and increase of less than 200%. While this slight theoretical increase may be beneficial, it has been unexpectedly determined that the actual increase in oxidative stability is greater than 400% ( and even as great as almost 2,300%, such as seen with macadamia nut oil. The ethyl esters of these fats and oils see an even greater increase (greater than 4,500%, as high as 8,285% for the ethyl macadamiate). This dramatic increase is extremely useful for compositions such as emollients since it extends the emollient shelf live significantly beyond that of any other natural, or naturally derived, emollient composition. Moreover, it has been surprisingly determined that further addition of a supplemental additive extends the oxidative stability even more.

Heretofore, it has been impossible to use substantial quantities of oil derivatives, such as the ethyl esters, in cosmetic formulations despite their beneficial "dry emollient" properties. Now that compositions have been produced that are ultra-stable, meaningful quantities of these materials can be used and, at the same time, the formulation will remain oxidatively stable. Thus, the present invention provides compositions displaying drastically improved oxidation resistance comprising oils and waxes, or derivatives thereof, not including the synthetic free-radical terminating antioxidants. The synthetic free-radical terminating antioxidants may be used in amounts from about 0.001% by weight of the composition to about 5% by weight of the composition, depending upon the particular formulation, and other additives in the composition. In general, relatively low amounts of the tocopherols are highly effective.

Further, it is expected that including into the composition of the present invention formulations that contain antioxidants, especially tocopherols, will further enhance the ultra-stability of the composition of the present invention. While there is a preferred range for the amount of free-radical terminating antioxidants added to the present invention as disclosed herein, additional antioxidants have been shown to further increase the stability (meaning that the stabilization effect has not leveled off).

The compositions of the present invention are found to be most useful as emollients in cosmetic applications including, but not limited to: creams, lotions, and liquid foundation; massage oils and the like; pressed products such as eye shadow, blush, and powder; molded products such as lipstick, lip balm, foundation, blush, eye liner, eye shadow, mascara and the like; hair care products, such as leave in conditioners, relaxers, hair dyes and other applications where there is stress on the oxidative stability of the composition.

In addition to the essential ingredients in the emollient compositions of the present invention, further material may be present in the composition for functional or aesthetic reason. Additional antioxidants from the classes described herein and/or antioxidants, including tocotrienols (compounds homologous to tocopherols that differ by the presence of three unsaturated bonds in the side chain), and oryzanol (a mixture of ferulic acid esters of sterols, e.g., beta-sitosteryl ferulate and methyl ferulate, and triterpene alcohols, e.g., 24-methylenecycloartenyl ferulate; see Bailey's Industrial Oil and Fat Products, 4$^{th}$ Ed., John Wiley, New York, 1979, volume 1, pages 407 to 409) may be present. Fragrances, colorants (e.g., dyes or pigments), topically applied medications, UV absorbers, whitening agents, emulsifying agents, binders, scrubbing particulates, and the like may be present.

Fatty elements in addition to the stabilized oil, waxes, or their derivatives that may be used can be selected from mineral oils like paraffin or petroleum oils, silicon oils, vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils, animal oils and fats like tallow, lanolin, butter oil, fatty acid esters, fatty alcohol esters, waxes whose melting point is the same as the skin's (animal waxes like bee's wax, carnauba or candelilla waxes, mineral waxes like micro-crystalline waxes and synthetic waxes like polyethylene or silicone waxes). All acceptable oils used in cosmetic formulation can be used, like the ones that have been mentioned in the CTFA's book, Cosmetic Ingredient Handbook, First edition, 1988, The Cosmetic, Toiletry and Fragrance Association, Inc., Washington (hereinafter, "CTFA").

Cosmetically or dermatologically active substances may be added to the compositions of the present invention, meaning active cosmetics chosen from anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances may represent from 1 to 20% by weight of the total weight of the composition.

Detergent or foaming agents, which may be added to the composition of the present invention, for example, may include disodic cocoamphodiacetate salts; lauroylether sulfosuccinate disodic salts; the vegetable protein acylates; the cocoyl gutamate triethanolamine salts; the lauroyl sarcosinate sodium salts; the glucoside decyl-ethers; and the sodium sulfate lauroyl ethers.

Pasty active compounds like lanolin by-products (acetyl lanolin, lanolin, and lanolin alcohols; cholesterol by-products, like cholesterol esters (12 cholesteryl hydroxy stearate); pantaerythritol hydroxylated esters, linear mono-esters like butyl stearate, arachidyl propionate or stearyl heptanoate, and triglycerides with a fatty chain less that C16 can also be used. These substances may be water-soluble, lipid-soluble, or lipid-soluble and water soluble at the same time, or dispersible. They can be chosen from the compounds that are found in the CTFA dictionary at pages 51 to 101.

Surface active agents, cationic, anionic, non-ionic and/or zwitterionic may be used in combination with the present invention. These surface active agents can be chosen, for example, from the hydrophilic surface agents, like glycols, such as hexylene glycol, butylene-1,2 glycol, ethyl-2-hexyl sulfosuccinate; oxyethylene octylphenol (9, and the salts derived from cocoyl and lauroyl collagen, sorbitan palmitate, and the polyoxyethylene byproducts of sorbitol palmitate esters, salts of fatty chain quaternary ammonium. Suitable anionic surfactants which may also be used include the water-soluble alkali metal or ammonium salts having alkyl radicals containing from abut 8 to about 22 carbon atoms, the term alkyl being used to include the alkyl portion of higher acyl radicals. Examples of suitable synthetic anionic surfactants are sodium or ammonium alkyl sulfates, especially those obtained by sulfating higher ($C_8$-$C_{18}$) alcohols produced, for example, from tallow or coconut oil; alkyl ($C_9$-$C_{20}$) benzene sulfonates, particularly sodium linear secondary alkyl ($C_{10}$-$C_{15}$) benzene sulfonates; alkyl glyceryl ether sulfates, especially those ethers of the higher alcohols derived from tallow or coconut oil and synthetic alcohols derived from petroleum; coconut oil fatty monoglyceride sulfates and sulfonates; salts of sulfuric acid esters of higher ($C_8$-$C_{18}$) fatty alcohol-alkylene oxide, particularly ethylene oxide reaction products; the reaction products of fatty acids such as coconut fatty acids esterified with isoethionic acid and neutralized with sodium hydroxide; sodium and potassium salts of fatty acid amides of methyl taurine; alkane monosulfonates such as those derived from reacting alpha-olefins ($C_8$-$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$-$C_{20}$ alpha-olefins, with $SO_3$ and then neutralizing and hydrolyzing the reaction product. The preferred anionic surfactants are sodium or ammonium ($C_{10}$-$C_{18}$) alkyl sulfates and ($C_{10}$-$C_{18}$) alkyl polyethoxy (1-11 EO, ethylene oxide) sulfates and mixtures thereof having differing water solubilities.

Particularly preferred anionic surfactants comprise a mixture of a $C_{10}$-$C_{18}$ alkyl sodium or ammonium sulfate or sulfonate or a $C_{14}$-$C_{18}$ alpha-olefin sodium or ammonium sulfonate (AOS) and a $C_8$-$C_{12}$ alkyl polyethoxy (2-4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also optional for use with the present invention.

The amount of anionic surfactant present in the composition, which is moringa oil (or its derivatives) combined with tocopherols, will generally range from about 0 or 1% or 4 to 12% by weight (total ingredients) by weight. The amphoteric or zwitterionic surfactant, may optionally be present at a level of at least abut 0.1 or at least about 0.25 percent by weight of the total composition, per 1 part by weight of the content of anionic surfactant present in the composition.

Examples of amphoteric surfactants that may be used in the composition of the invention are betaines and compounds that can be broadly described as derivatives of aliphatic secondary and tertiary amines in which the aliphatic radical can be straight chain or branched and wherein one of the aliphatic substituent contains from abut 8 to 18 carbon atoms and one contains an ionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, N-higher alkyl aspartic acids and the products sold under the trade name "Miranol".

Makeup or cosmetic compositions comprising the present invention may also contain as an optional ingredient, a film forming skin tightening agent, particularly a plant derived biological polysaccharide cosmetic ingredient that may be combined with a casein hydrolysate.

The polysaccharides that can be used in the practice of the invention include, for example, lecithin, pectin, karaya gum, locust bean gum, xanthan gum and mixtures thereof. The polysaccharides are preferably used in the present compositions in combination with a casein hydrolysate.

Suitable co-emulsifiers are both known w/o (water in oil) and o/w (oil in water) emulsifiers. Typical examples of fats are glycerides while suitable waxes include inter alia beeswax, paraffin wax or microwaxes. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, also fatty alcohols, monoglycrides and fatty acids, polyacrylates, polyvinyl alcohol and polyvinyl pyrrolidone. In the context of the invention, biogenic agents are, for example, plant extracts, protein hydrolyzates and vitamin complexes. Typical film formers are, for example, polyvinyl pyrolidone, vinyl pyrolidone/vinyl acetate copolymers, polymers of the acrylic acid series, quaternary cellulose derivatives and similar compounds. Suitable preservatives are, for example formaldehyde solution, p-hydroxybenzoate or sorbic acid. Suitable pearl esters are, for example, glycol distearic acid esters, such as ethylene glycol distearate, and also fatty acids and fatty acid monoglycol esters. The dyes used may be selected from many of the substances that are permitted and suitable for cosmetic purposes, as listed for example in the publication "Kosmetische Farbemittel" of the Farbstoffkommission der Deutschen pages 81-106. These dyes are typically used in concentrations of 0.001 to 0.1% by weight, based on the mixture as a whole.

The total percentage content of auxiliaries and additives may be 1 to 50% by weight and may be 5 to 40% by weight, based on the formulation. The formulations may be produced in known manner, i.e. for example by hot, cold, ho-hot/cold or PIT emulsification. These are purely mechanical processes that do not involve a chemical reaction. The cosmetic and/or pharmaceutical formulations may have a water content of 25 to 95% by weight and preferably 50 to 75% by weight.

The preferred embodiment of the invention is described in the following table and Detailed Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

TABLE 1

| Sample | % Methylene Interruption | OSI with No Additional Antioxidants (in hours) | OSI with Propyl Gallate/ (Percentage Increase) | OSI with BHA/ (Percentage Increase) | OSI with BHT/ (Percentage Increase) | OSI with TBHQ/ (Percentage Increase) |
|---|---|---|---|---|---|---|
| Moringa oil | 0.7 | 29.6 | 407.9/ 1,278% | 90.5/ 206% | 65.4/ 121% | 83.1/ 181% |
| Ethyl Moringate | 0.7 | 5.1 | 212.5/ 4,067% | 29.2/ 473% | 24.1/ 373% | 17.2/ 237% |
| Meadowfoam Oil | 0.6 | 69.1 | 246.8/ 257% | 77.0/ 11% | 96.0/ 39% | 166.6/ 141% |
| Ethyl Meadowfoamate | 0.6 | 48.7 | 70.1/ 44% | 107.1/ 120% | 71.0/ 46% | 93.3/ 92% |
| Babassu Oil | 1.5 | 46.5 | 567.0/ 1,119% | 125.3/ 170% | 107.2/ 131% | 264.0/ 468% |
| Ethyl Babassuate | 1.5 | 5.4 | 28.8/ 433% | 65.4/ 1,113% | 24.6/ 356% | 24.6/ 356% |
| Macadamia oil | 3.5 | 5.6 | 134.1/ 2,295% | 54.6/ 875% | 32.9/ 488% | 67.3/ 1,102% |
| Ethyl Macadamiate | 3.5 | 1.4 | 117.4/ 8,286% | 38.5/ 2,650% | 14.4/ 929% | 8.4/ 500% |
| Cottonseed* oil | 49.6 | 5.4 | 10.1/ 87% | 6.2/ 15% | 6.6/ 22% | |
| Canola oil | 28.3 | 9.3 | 27.4/ 195% | 11.6/ 25% | 15.8/ 70% | 66.4/ 614% |
| Ethyl Canolate | 28.3 | 0.9 | 0.9/ 0 | 0.9/ 0 | 0.9/ 0 | 5.3/ 489% |
| Soybean* oil | 58.6 | 5.7 | 12.6/ 121% | 6.2/ 9% | 7.2/ 26% | |
| High-Oleic Safflower* oil | 13.7 | 12.5 | 32.6/ 161% | 15.9/ 27% | 16.0/ 28% | |
| Traditional Sunflower Oil | 66.9 | 4.6 | 12.5/ 172% | 5.6/ 22% | 7.0/ 52% | 25.5/ 454% |
| Ethyl Sunflowerate (Trad) | 66.9 | 1.4 | 0.9/ −64% | 1.9/ 36% | 2.8/ 100% | 12.5/ 793% |
| High-oleic Sunflower* oil | — | 14.0 | 39.0/ 179% | 17.7/ 26% | 17.8/ 27% | |
| High-Oleic | 4.0 | 28.1 | 134.1/ | 42.7/ | 40.4/ | 111.8/ |

TABLE 1-continued

| Sample | % Methylene Interruption | OSI with No Additional Antioxidants (in hours) | OSI with Propyl Gallate/ (Percentage Increase) | OSI with BHA/ (Percentage Increase) | OSI with BHT/ (Percentage Increase) | OSI with TBHQ/ (Percentage Increase) |
|---|---|---|---|---|---|---|
| Sunflower** oil | | | 377% | 52% | 44% | 298% |
| Ethyl Sunflowerate | 4.0 | 2.2 | 97.9/ 4,350% | 27.8/ 1,164% | 6.5/ 196% | 3.2/ 46% |

*(from Eastman)
**(from Floratech)

What is claimed is:

1. An emollient composition suitable for topical application, said composition comprising:
    a long-chain oil selected from the group consisting of moringa oil, its ethyl ester derivatives, and combinations thereof, wherein said long-chain oil has a percent methylene interrupted unsaturation which is less than about 5%; and
    a tocopherol and a synthetic free-radical terminating antioxidant selected from the group consisting of butylated hydroxytoluene, butylated hydroxyanisole, propyl gallate, a hydroquinone, and combinations thereof, wherein the tocopherol and synthetic free-radical terminating antioxidant provide an oxidative stabilization to the long-chain oil of more than 400% relative to the oxidative stability of the oil alone.

2. The composition according to claim 1 wherein the tocopherol and synthetic free radical-terminating antioxidant are present in an amount of from about 0.01% to about 5.0% by weight of said long chain oil.

3. The composition according to claim 1 further comprising a reducing agent present in an amount of from 0.001 to 2% by weight, wherein the reducing agent is selected from the group consisting of ascorbic acid, ascorbic acid esters, ascorbyl esters, sulfites, glucose oxidase comprising catalase, erythrobic acid and combinations thereof.

4. An emollient composition suitable for topical application, said composition comprising:
    a long-chain oil selected from the group consisting of moringa oil, its ethyl ester derivatives, and combinations thereof, wherein said long-chain-oil has a methylene interrupted unsaturation which is less than about 5%; and
    a synthetic free radical-terminating antioxidant selected from the group consisting of butylated hydroxytoluene, butylated hydroxyanisole, propyl gallate, a hydroquinone, and combinations thereof, wherein said synthetic free-radical-terminating antioxidant is present in an amount of from about 0.01% to about 50% by weight of said long-chain oil, and wherein said synthetic free-radical-terminating antioxidant provides an oxidative stabilization to the long-chain oil greater than 400% relative to the oxidative stability of the oil alone.

5. The composition according to claim 4 further comprising a reducing agent present in an amount of from 0.001 to 20% by weight wherein said reducing agent is selected from the group consisting of ascorbic acid, ascorbic acid esters, ascorbyl esters, sulfites, glucose oxidases comprising catalase, erythorbic acid, and combinations thereof.

6. The composition of claim 4 further comprising one or more tocopherols.

* * * * *

UNITED STATES PATENT AND TRADEMARK OFFICE
CERTIFICATE OF CORRECTION

| | |
|---|---|
| PATENT NO. | : 7,691,397 B2 |
| APPLICATION NO. | : 10/410787 |
| DATED | : April 6, 2010 |
| INVENTOR(S) | : James H. Brown et al. |

It is certified that error appears in the above-identified patent and that said Letters Patent is hereby corrected as shown below:

Column 14, line 27 claim 4 - 0.01% should be changed to 0.001%

Column 14, line 27 claim 4 - 50% should be changed to 5%

Column 14, line 34 claim 4 - 20% should be changed to 2%

Signed and Sealed this

First Day of June, 2010

David J. Kappos
*Director of the United States Patent and Trademark Office*